(12) United States Patent
Lever et al.

(10) Patent No.: US 6,639,116 B2
(45) Date of Patent: Oct. 28, 2003

(54) SIMPLIFIED METHODS OF MAKING 1,3-CYCLOHEXADIENE

(75) Inventors: John G. Lever, Spartanburg, SC (US); Kenneth Wagner, Gainesville, FL (US); John C. Sworen, Gainesville, FL (US)

(73) Assignee: Millken & Company, Spartanburg, SC (US)

( * ) Notice: Subject to any disclaimer, the term of this patent is extended or adjusted under 35 U.S.C. 154(b) by 18 days.

(21) Appl. No.: 10/099,402

(22) Filed: Mar. 15, 2002

(65) Prior Publication Data

US 2003/0176749 A1 Sep. 18, 2003

(51) Int. Cl.⁷ .............................. C07C 6/04; C07C 6/03
(52) U.S. Cl. ...................... 585/364; 585/643; 585/644; 585/646; 585/647; 585/366
(58) Field of Search ................... 585/643, 644, 585/646, 647, 364, 366

(56) References Cited

FOREIGN PATENT DOCUMENTS

| | | |
|---|---|---|
| JP | 5304417 | 11/1993 |
| JP | 05307623 | 11/1993 |
| JP | 5308846 | 11/1993 |
| JP | 06154940 | 6/1994 |
| JP | 7-157445 | * 6/1995 |
| JP | 11201958 | 7/1999 |

* cited by examiner

Primary Examiner—Thuan D. Dang
(74) Attorney, Agent, or Firm—Terry T. Moyer; William S. Parks

(57) ABSTRACT

Novel condensation reactions used to produce 1,3-cyclohexadiene. Such a compound is an important precursor in the manufacture of high performance plastics, as one example, are provided. In the past, the production methods for such 1,3-cyclohexadiene required very complex reactions involving numerous process steps. Such a method has proven costly, difficult to properly monitor and control, and less than reliable to provide even low amounts of such a precursor compound. The inventive production methods thus permit a reduction in complexity and cost, and, with a single reaction step, facilitate quality measurements as to the product purity itself.

20 Claims, No Drawings

SIMPLIFIED METHODS OF MAKING 1,3-CYCLOHEXADIENE

FIELD OF THE INVENTION

This invention relates to novel condensation reactions used to produce 1,3-cyclohexadiene. Such a compound is an important precursor in the manufacture of high performance plastics, as one example. In the past, the production methods for such 1,3-cyclohexadiene required relatively complex, multi-step reactions. Such a method has proven costly, difficult to properly monitor and control, and less than reliable to provide even low amounts of such a precursor compound. The inventive production methods thus permit a reduction in complexity and cost, and, with a single reaction step, the ability to produce the target molecule.

BACKGROUND OF THE PRIOR ART

All U.S. patents cited within this specification are hereby incorporated by reference.

Cyclohexadiene is utilized for a wide variety of applications, primarily as a monomer in the production of polycyclohexadiene, a component within high performance plastics. Unfortunately, the high cost of producing 1,3-cyclohexadiene has precluded widespread utilization in these and other areas, as well as more extensive use within its common applications. In particular, the processes historically available for 1,3-cyclohexadiene production involve at least two separate process steps or requiring very high temperatures or expensive materials, such as precursors, catalysts, reactants, and the like, which add to the cost and complexity thereof. As a result, cost has been the main driver at preventing more widespread introduction of such a compound within a broad variety of production methods and end-uses.

As examples of previous production methods for 1,3-cyclohexadiene, the following are noted, all Japanese patent documents and all attributable to Asahi Chemical Industries, Inc.: in Japanese Patent Abstract 06154940, cyclohexene is reacted with nitrous oxide over a silica catalyst at elevated temperatures to produce the desired diene; in Japanese Patent Abstract 11201958, 1,2-dihalocyclohexane is reacted with a bipolar nonprotic solvent and a base, all while water is added to the system and the reaction is performed at elevated temperatures (these two reactions produce low-purity grades of the desired cyclohexadiene product); in Japanese Patent 1993-308846, gas-phase dehydration of 2-cyclohexen-1-ol is performed, within a mixture of cyclohexene oxide and 2-cyclohexen-1-one, in the presence of a small amount of cyclohexenyl hydroperoxide and a phosphate catalyst; in Japanese Patent 1993-304417, cyclohexene is removed from distillation or absorptive separation from a mixture include that material as well as 2-cyclohexen-1-ol, cyclohexene oxide, and 2-cyclohexen-1-one, and is subsequently dehydrated in vapor phase at elevated temperatures (in the presence of a phosphoric acid salt catalyst), the product of which is eventually purified through further distillation of the high-boiling components therefrom; in Japanese Patent Abstract 05307623, initially cyclohexene is oxidized to form a mixture of cyclohexene hydroperoxide and cyclohexene, and then causing an epoxidation reaction between these two components to form a mixture of 2-cyclohexen-1-ol, cyclohexene oxide, cyclohexene, and 2-cyclohexen-1-one, after which the cyclohexene is removed and dehydrated to form 1,3-cyclohexadiene; and other disclosures discussing the utilization of high purity phosphate catalysts, suppressing the production of inseparable components within reaction systems of cyclohexene-based reactants for higher purity filtration capabilities, and other like methods of purifying the initial reactants. As is evident, such reactions are complex, while others generate low-purity products in mixtures that are difficult to effectuate proper separation for collection of the desired diene. It is thus evident that a better procedure in terms of complexity, at least, is needed to permit production of such an important compound. To date, the aforementioned methods are, unfortunately, the most effective methods currently known within the industry.

OBJECTS OF THE INVENTION

Therefore, one of the objects of the invention is to provide a simple method of producing 1,3-cyclohexadiene in a single step and at very low temperatures. Another object of this invention is to provide a synthetic route for 1,3-cyclohexadiene involving the introduction of a heavy metal catalyst and exposing the entire reaction to sub-freezing temperatures.

Accordingly, this invention encompasses a method of producing 1,3-cyclohexadiene comprising the process steps of providing a non-conjugated diene, triene, or polyene, preferably a cyclic diene or triene, and most preferably a 1,5-based diene or triene of this type (such as 1,5-cyclooctadiene or 1,5,9-cyclododecatriene, for instance) and reacting said diene or triene with a conjugated aliphatic compound, preferably 1,3-butadiene, in molar relation thereto in the presence of a heavy metal-containing catalyst, preferably, though not necessarily at a temperature of below 20° C. (higher temperatures may be utilized if such permits quicker reaction). Also encompassed within this invention is the method comprising the process steps of first providing the aforementioned non-conjugated diene or triene in the presence of 1,3-butadiene and reacting the two components in the presence of a heavy metal-containing catalyst, such as ruthenium-based second generation Grubbs catalyst [e.g., tricylohexylphosphine[1,3-bis(2,4,6-trimethylphenyl)-4,5-dihydroimidazol-2-ylidene][benzylidine]ruthenium (IV) dichloride], for example.

Such an inventive method is a one-step metathesis condensation reaction that requires performance of the catalyst in such a manner as to act as an impetus to condensation of the two starting materials (e.g., non-conjugated diene or triene and 1,3-butadiene) rather than acting to polymerize or copolymerize these starting materials. Such heavy metal-based catalysts (e.g., second generation Grubbs ruthenium-based catalyst) are utilized generally for polymerization metathesis reactions and perform very well in such reactions. Without intending to be limited to any specific scientific theory, it is believed that the selected catalysts also effectuate polymerization of the non-conjugated monomers generated from the opening of the preferred cyclic diene or triene starting materials. It is further believed that the resultant polyenes (in this situation, having at least 4 repeating units in non-conjugated relation to each other) also have the ability to react with the required conjugated aliphatic compound to produce the desired 1,3-cyclohexadiene end product in the presence of such catalysts as well. Thus, it is further believed that polyenes alone, such as, as one non-limiting example, poly(1,5-butadiene), may function properly within this inventive method.

Surprisingly, then, it has been determined that such catalysts can function as needed within a condensation metathesis reaction to form 1,3-cyclohexadiene from the two aforementioned types of starting materials, in a one-step procedure at an acceptable yield, and most importantly, with high resultant purity thereof. Thus, a method of producing 1,3-cyclohexadiene has been accorded the pertinent industries utilizing readily available, inexpensive starting materials, which can also be practiced at very low temperatures, all to provide a cost-effective, simplified procedure for such purpose. Furthermore, in a potentially preferred embodiment of such a method, the desired 1,3-cyclohexadiene product is made in relatively high levels and in formulations which can easily be purified through removal of gaseous ethylene therefrom.

The preferred non-conjugated diene is 1,5-cyclooctadiene (and possibly 1,5-hexadiene, and the preferred non-conjugated triene is 1,5,9-cyclododecatriene. Other possible catalysts, without limitation, include metal-containing types including metals from Group IVA, such as titanium-, and zirconium-based compounds; Group VA metals, such as vanadium-, niobium-, and tantalum-based compounds; Group VIA metals, such as chromium-, molybdenum-, tungsten-; Group VIIA metals, such as technetium-, and rhenium-based compounds; and Group VIII metals, including cobalt-, osmium-, rhodium- and iridium-based compounds. Mixtures of such catalysts, as well as catalysts including multiple types of metal components may also be utilized for such purpose, and such mixtures or combinations of metals are thus encompassed within the term "catalyst" as it pertains to this invention. Such catalyst systems include those noted at pages 19–44 of *Olefin Metathesis and Metathesis Polymerization, Survey of Catalyst Systems*, by K. J. Ivin and J. C. Mol, Academic Press (1997). Of these, the compounds based upon Group VIII metals are preferred with ruthenium-based compounds most preferred.

The result of such reactions is the desired production of 1,3-cyclohexadiene, specifically in composition with ethylene that is, as noted above, easily separated therefrom to produce a high purity compound, if desired. As a result, such a reaction also provides an ability to produce useful amounts of such a co-product (ethylene) that may be collected and utilized as desired. The temperature range for such a reaction is between about −30° C. and 100° C., more preferably, for cost-reduction purposes only, between −25 and 40°, still more preferably between −20 and 10° C., and most preferably about −20° C. Again, If the diene is utilized as a starting material, the 1,3-butadiene is added in at least 2 molar equivalent thereto; for the triene, the butadiene reactant is present in at least 3 molar equivalent. In such situations, the resultant products are either 2 molar 1,3-cyclohexadiene with 2 molar ethylene (for the diene starting material) or 3 molar of each (for the triene starting material).

Such condensation reactions have heretofore not been performed for the production of 1,3-cyclohexadiene, specifically such reactions that rely upon the presence of excellent catalysts therein. The aforementioned Group VIII-based catalysts, such as, as one non-limiting example, ruthenium-based second generation Grubbs catalyst, the structure of which conforms with the structure of Formula (I):

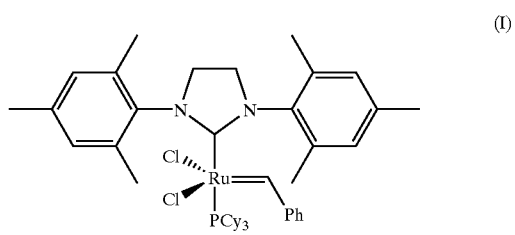

are the most preferred for this purpose. As alluded to above, such catalysts are relatively new to begin with, although they have been taught as possible catalysts for general metathesis condensation reactions to form various types of unsaturated hydrocarbon compounds. The introduction of such catalysts with specific 1,5-cyclooctadiene or 1,5,9-cyclododecatriene is simply not a suggestion that has been made in the past, particularly in combination with 1,3-butadiene, to form 1,3-cyclohexadiene in an extremely low-temperature process. As noted previously, the traditional and typical methods of producing 1,3-cyclohexadiene involved the utilization of cyclohexene-based precursors to which a second double bond is provided in conjugated relation to the initial unsaturated location. Thus, the inventive method is clearly novel as a non-cyclohexene-based compound is utilized to produce 1,3-cyclohexadiene in a single-step procedure.

DESCRIPTION OF THE PREFERRED EMBODIMENTS

Without limiting the scope of the invention, the preferred features of the invention are hereinafter set forth.

I. Condensation of 1,3-Butadiene with 1,5-Cyclooctadiene Under Reflux Conditions 0.053 g of tricylohexylphosphine[1,3-bis(2,4,6-trimethylphenyl)-4,5-dihydroimidazol-2-ylidene] [benzylidine]ruthenium (IV) dichloride (second generation Grubbs catalyst) were added to a 100 mL, 3-neck round bottom flask. A cold finger and septum were attached, and a gas line for the entry of butadiene was added. A nitrogen line was attached to the cold finger and the entire system was allowed to purge for fifteen minutes. A dry ice/acetone bath was prepared and placed underneath the flask, and the same mixture was added to the cold finger as well. After cooling down for approximately 10 minutes to a temperature of about 0° C., 2.6 mL of tetradecane (internal standard) and 5.8 mL (0.046 mol) of 1,5-cyclooctadiene were added to the reaction flask. The nitrogen line was closed and butadiene was allowed to condense into the system until approximately 5 g (0.092 mol) had collected. The butadiene line was closed and nitrogen was again allowed to flow through the system. The ice bath was removed from the bottom of the flask, and the butadiene was allowed to reflux throughout the reaction. The reaction was monitored after 10 min and 1 hr by GC-MS analysis. Aliquots for GC-MS analysis were prepared by diluting 0.5 mL of the reaction sample with 0.5 mL of acetonitrile. Under such gas chromatography/mass spectrometer analysis, the yield of 1,3-cyclohexadiene produced after 10 minutes was about the same as after 1 hour, roughly 22–23%.

II. Metathesis Condensation of 1,3-Butadiene with 1,5-Cyclooctadiene in the Presence of Second Generation Grubbs Catalyst at −20° C.

2.0 g of tetradecane were added to a 3-neck, round bottom flask. A cold finger and septum were attached and a gas line for the entry of butadiene was added. A nitrogen line was attached to the cold finger and the entire system was purged for fifteen minutes. A dry ice/acetone mix was added to the cold finger and butadiene was allowed to condense into the flask until approximately 5 g (0.092 mol) had collected. The butadiene line was turned off and nitrogen flow was restored to the flask. An ethylene glycol/dry ice bath was placed underneath the flask and the temperature was kept at −20° C. 5.7 mL (0.046 mol) of 1,5-cyclooctadiene were then added to the flask via syringe and 0.05 g of second generation Grubbs catalyst were added to the flask. The reaction was allowed to run undisturbed, and dry ice was added periodically to ensure that the flask was kept at −20° C. The reaction was monitored at 10 min, 1 hr, and 3 hr by GC-MS analysis. Under such gas chromatography/mass spectrometer analysis, the yield of 1,3-cyclohexadiene produced after 10 minutes, 1 hour, and 3 hours, increased from 5 to 10 to 19%.

III. Condensation of 1,3-Butadiene with 1,5,9-Cyclododecatriene in the Presence of Second Generation Grubbs Catalyst at −20° C.

The same materials, conditions, etc., were followed as in II., above, except that 1,5,9-cyclododecatriene was utilized in place of 1,5-cyclohexadiene. The reaction was monitored at 10 min and 2 hours by GC-MS analysis. Under such gas chromatography/mass spectrometer analysis, the yield of 1,3-cyclohexadiene produced after 10 minutes and 2 hours were similar, about 15 and 11%, respectively.

Thus, it is evident that the above inventive condensation reactions permit a unique, one-step procedure at low temperature levels to produce 1,3-cyclohexadiene.

There are, of course, many alternate embodiments and modifications of the present invention which are intended to be included within the spirit and scope of the following claims.

What is claimed is:

1. A method of producing a 1,3-cyclohexadiene comprising the reaction of a non-conjugated diene, triene, or polyene, and a conjugated aliphatic compound in molar relation thereto in the presence of a heavy metal-containing catalyst.

2. The method of claim 1 wherein said non-conjugated diene, triene, or polyene is 1,5-based.

3. The method of claim 2 wherein said non-conjugated diene is 1,5-cyclooctadiene and wherein said conjugated aliphatic compound is 1,3-butadiene.

4. The method of claim 2 wherein said non-conjugated cyclic triene is 1,5,9-cyclododecatriene and said conjugated aliphatic aliphatic compound is 1,3-butadiene.

5. The method of claim 1 wherein said heavy metal-containing catalyst comprises at least one metal selected from the group consisting of at least one Group IV-A metal, at least one Group V-A metal, at least one VI-A metal, at least one Group VII-A metal, at least one Group VIII metal, and any combinations of said metals within individual catalysts.

6. The method of claim 5 wherein said at least one metal is selected from the group consisting of titanium, zirconium, vanadium, niobium, tantalum, chromium, molybdenum, tungsten, technetium, rhenium, cobalt, osmium, rhodium, ruthenium, and iridium, and any combinations thereof.

7. The method of claim 6 wherein said at least one metal is selected from the group consisting of ruthenium, cobalt, osmium, indium, rhodium, and any combinations thereof.

8. The method of claim 7 wherein said catalyst is ruthenium-based second generation Grubbs catalyst.

9. The method of claim 1 wherein the temperature of said reaction is at most 20° C.

10. The method of claim 9 wherein the temperature of said reaction is about −20° C.

11. The method of claim 3 wherein said heavy metal-containing catalyst comprises at least one Group VIII metal therein.

12. The method of claim 11 wherein said at least one metal is selected from the group consisting of ruthenium, cobalt, osmium, indium, rhodium, and any combinations thereof.

13. The method of claim 12 wherein said catalyst is ruthenium-based second generation Grubbs catalyst.

14. The method of claim 13 wherein the temperature of said reaction is at most 20° C.

15. The method of claim 14 wherein the temperature of said reaction is about −20° C.

16. The method of claim 4 wherein said heavy metal-containing catalyst comprises at least one Group VIII metal therein.

17. The method of claim 16 wherein said at least one metal is selected from the group consisting of ruthenium, cobalt, osmium, indium, rhodium, and any combinations thereof.

18. The method of claim 17 wherein said catalyst is ruthenium-based second generation Grubbs catalyst.

19. The method of claim 18 wherein the temperature of said reaction is at most 20° C.

20. The method of claim 19 wherein the temperature of said reaction is about −20° C.

* * * * *